United States Patent [19]
Aoyama et al.

[11] Patent Number: 5,540,842
[45] Date of Patent: Jul. 30, 1996

[54] METHOD OF PRODUCING AN ARTIFICIAL KIDNEY PERFUSION COMPONENT FOR BICARBONATE DIALYSIS AND THE ARTIFICIAL KIDNEY PERFUSION COMPONENT

[75] Inventors: Hideyuki Aoyama, Tokushima; Hisao Mukai, Naruto; Kazuya Murakami, Tokushima, all of Japan

[73] Assignee: Tomita Pharmaceutical Co., Ltd., Naruto, Japan

[21] Appl. No.: 165,478

[22] Filed: Dec. 13, 1993

[30] Foreign Application Priority Data

Dec. 14, 1992 [JP] Japan .................................. 4-353965

[51] Int. Cl.⁶ .................................. A61K 9/00; A61K 9/14; A61K 33/06; A61K 33/14
[52] U.S. Cl. .......................... 210/647; 210/542; 210/646; 252/1; 252/183.16; 424/400; 424/489; 424/490; 424/600; 424/679; 424/680; 424/681; 424/717; 514/951
[58] Field of Search .................................. 210/645, 647, 210/646, 542; 252/1, 183.16; 424/400, 489, 600, 717, 679, 680, 681, 490; 435/2; 436/17; 514/951

[56] References Cited

U.S. PATENT DOCUMENTS

| | | | |
|---|---|---|---|
| 4,655,941 | 4/1987 | Suzuki | 252/1 |
| 4,678,661 | 7/1987 | Gergely et al. | 424/44 |
| 4,756,838 | 7/1988 | Veltman | 252/1 |
| 5,071,558 | 12/1991 | Itob | 210/542 |
| 5,122,516 | 6/1992 | Watanabe et al. | 210/646 |

FOREIGN PATENT DOCUMENTS

| | | |
|---|---|---|
| 177614 | 4/1986 | European Pat. Off. . |
| 399918 | 11/1990 | European Pat. Off. . |
| 417478 | 3/1991 | European Pat. Off. . |
| 2628318 | 9/1989 | France . |
| WO92/16117 | 10/1992 | WIPO . |

*Primary Examiner*—John Kim
*Attorney, Agent, or Firm*—Larson and Taylor

[57] ABSTRACT

A granular to fine-granular dry mix powder (an artificial kidney perfusion component A of uniform composition) for use in the preparation of an artificial kidney perfusion fluid for bicarbonate dialysis and a method of producing the same.

A granular to fine-granular Composition A comprising granules each comprised of a plurality of NaCl grains carrying KCl, $CaCl_2$, $MgCl_2$ and sodium acetate adhered to the surface of each grain.

NaCl, KCl $CaCl_2$, $MgCl_2$ and sodium acetate are mixed in the presence of not less than 10 weight parts of water based on 100 weight parts of sodium acetate and the resultant mixture is heated at not less than 50° C. to bring the sodium acetate into a transiently molten state and mixing acetic acid with the same mixture.

9 Claims, 1 Drawing Sheet

METHOD OF PRODUCING AN ARTIFICIAL KIDNEY PERFUSION COMPONENT FOR BICARBONATE DIALYSIS AND THE ARTIFICIAL KIDNEY PERFUSION COMPONENT

FIELD OF THE INVENTION

The present invention relates to a method of producing an artificial kidney perfusion component for bicarbonate dialysis and the artificial kidney perfusion component.

BACKGROUND OF THE INVENTION

As the artificial kidney perfusion fluid for bicarbonate dialysis (hereinafter referred to briefly as bicarbonate dialyzate), an aqueous system prepared by blending two artificial kidney perfusion components, i.e. the so-called Component A comprising electrolytes, namely sodium chloride, potassium chloride, calcium chloride, magnesium chloride and sodium acetate, optionally supplemented with glucose, and the so-called Component B comprising a powder or an aqueous solution of sodium bicarbonate is generally employed.

For reference, the amounts of said respective ingredients contained in each 10 liters of the bicarbonate dialyzate in common use are shown in Table 1.

TABLE 1

| <Component A> | |
| --- | --- |
| Sodium chloride | 1943.1~2238.0 g |
| Potassium chloride | 26.1~104.4 g |
| Calcium chloride | 25.7~102.9 g |
| Magnesium chloride | 17.8~71.2 g |
| Sodium acetate | 57.42~344.5 g |
| Glucose | 0~700 g |
| <Component B> | |
| Sodium bicarbonate | 588.1~928 g |

Regarding Component B, both a solution form and a powdery form have been developed for selective use. As to Component A, which is a mixture of several ingredients, it is difficult to provide a powder of uniform composition. At the present time, therefore, an aqueous solution is manufactured and packaged in polyethylene bottles of about 10 l capacity in the factory and shipped to hospitals and dialysis centers. However, because Component A in the solution form is substantial in weight and volume, it is not satisfactory from the standpoint of shipping cost and storage space available in hospitals and so on. Moreover, it is undesirable in view of the problems associated with the disposal of polyethylene bottles after use.

As the pulverization technology for Component A, the dry granulation method comprising mix-pulverizing the electrolyte compounds and the wet granulation method comprising granulating and drying a slurry of the electrolyte compounds are known. However, these physical pulverizing and granulating methods are disadvantageous in that the charge tends to be contaminated with foreign matter due to friction with the equipment in the course of pulverization and granulation.

Moreover, the powder obtained by the known dry granulation method has the drawback that since the respective electrolyte compounds vary in hardness and some of them are readily pulverized while others are not and, hence, the former can be more readily granulated than the latter, a large difference in composition tends to occur between the recovered granulation and the powdery residue. In other words, the ratio of the respective electrolyte compounds in the charge formulation is sometimes at odds with their ratio in the final granulation and it happens at times that some electrolyte compounds must be supplementally added after granulation to correct for deficiencies.

As a means for overcoming this disadvantage, there has been proposed a method which comprises comminuting the respective electrolyte compounds into fine particles to increase the hardness of the resultant granulation and reduce the amount of powdery residues. However, it takes a time-consuming procedure to finely divide electrolyte compounds and in order to reduce the amount of powdery residues, a repeated granulation cycle is required but the practice increases the chance for the electrolyte compounds to be contaminated with foreign matter arising from frictional attrition of the pulverizing and granulating hardware.

As to the wet-granulation method, coagulation on drying tends to produce blocks which have to be crushed prior to final size selection so that the production process is complicated and unsuited for mass production.

OBJECTS OF THE INVENTION

It is an object of the invention to provide a novel method of producing a dry mix powder of Component A (artificial kidney perfusion Component A) which is for use as a component of the bicarbonate dialyzate system (artificial kidney perfusion fluid for bicarbonate dialysis).

It is another object of the invention to provide a powder of Component A which is uniform in composition.

SUMMARY OF THE INVENTION

After an intensive research undertaken to overcome the above-mentioned disadvantages of the prior arts, the inventor of the present invention discovered that intrinsically pure electrolyte compounds can be granulated without risks for contamination by a thermal mixing process which ingeniously takes advantage of the solubilities and hot-melt behaviors of electrolyte compounds which are to constitute a bicarbonate dialyzate.

The present invention is directed to a method of producing an artificial kidney perfusion component (Component A) for the preparation of an artificial kidney perfusion fluid for bicarbonate dialysis (bicarbonate dialyzate), which is a dry mix powder comprising sodium chloride, potassium chloride, calcium chloride, magnesium chloride and sodium acetate as electrolyte compound and glucose as an optional ingredient, characterized by mixing said electrolyte compounds in the presence of not less than 10 parts by weight, preferably not less than 20 parts by weight, of water (inclusive of the water of crystallization which may be bound to sodium acetate) based on 100 parts by weight of sodium acetate (as anhydride), heating the resultant mixture at a temperature of not less than 50° C., preferably not less than 60° C., to bring the sodium acetate into a transiently molten state and adding acetic acid to said mixture.

More particularly, the invention is directed to a method of producing said artificial kidney perfusion component (Component A) for preparation of a bicarbonate dialyzate characterized by comprising (1) a stage in which potassium chloride is dissolved in a specified amount of water, (2) a stage in which calcium chloride and magnesium chloride are dissolved in the resultant concentrated potassium chloride solution to cause precipitation of said potassium chloride, (3) a stage in which the resultant potassium chloride suspension is mixed with sodium chloride when hot, and (4) a stage in which the resultant mixture is mixed with sodium acetate in the presence of not less than 10 parts by weight of water (inclusive of the water of crystallization which may be bound to sodium acetate) based on 100 parts by weight of sodium acetate (as anhydride), the resultant mixture is heated at a temperature of not less than 50° C. to bring the sodium acetate into a transiently molten state and the mixture is mixed with acetic acid.

The invention is further directed to an artificial kidney perfusion component (Component A) for preparation of bicarbonate dialyzate in the form of granules or fine granules each comprised of a plurality of grains of sodium chloride carrying potassium chloride, calcium chloride, magnesium chloride and sodium acetate on the surface.

DETAILED DESCRIPTION OF THE INVENTION

Figure 1:
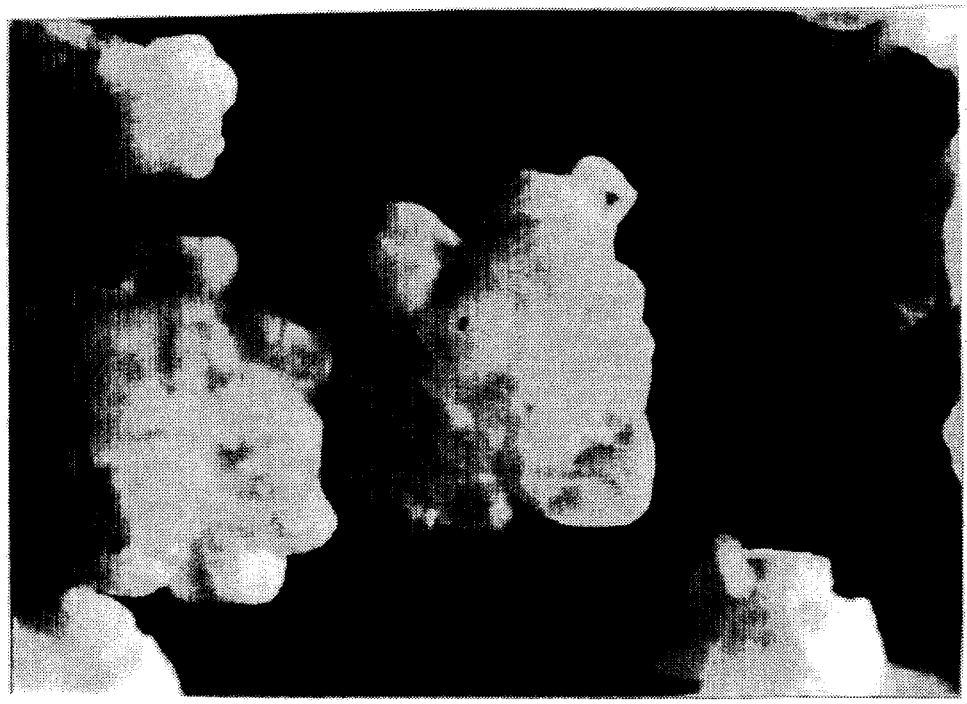
FIG. 1 is a microphotograph showing an example of the artificial kidney perfusion component for preparation of bicarbonate dialyzate according to the invention.

The artificial kidney perfusion component (Component A) of the present invention is a dry mix powder comprising electrolyte compounds, namely sodium chloride, potassium chloride, calcium chloride, magnesium chloride and sodium acetate, as essential ingredients and glucose as an optional ingredient. The Component A of the invention comprises crystal grains of sodium chloride and a compositionally uniform coating of other electrolyte compounds, with or without inclusion of glucose, as deposited thereon and binding pluralities of crystal grains of sodium chloride together to form granules (or fine granules).

In the Component A of the invention, the proportions of the granule-constituent respective ingredients are substantially uniform among the granules and within definite ranges. Therefore, the concentrations of the respective electrolyte compounds in the solution prepared by dissolving the Component A of the invention in a given quantity of water characteristically show a constant ratio. Therefore, when the dry mix Component A of the invention is put to use, that is to say dissolved in water, to provide an aqueous solution, it is not necessary to correct for the concentrations of the electrolyte compounds.

The Component A of the invention can be produced by mixing the electrolyte compounds, with or without addition of glucose, in the presence of a specified amount of water and bringing at least the sodium acetate, among the electrolyte compounds, into a transiently molten state (into a molten state for a while). In the method of producing said Component A in accordance with the invention, water is used in a proportion of not less than 10 parts by weight, preferably not less than 20 parts by weight and, for still better results, 20 to 70 parts by weight relative to 100 parts by weight of sodium acetate. When the proportion of water is too small, it is difficult to bring the sodium acetate into a molten state and, hence, to form a compositionally uniform coating layer. On the other hand, the use of an excess of water does not add to the intended effect but rather tends to cause the problem of retarded drying in the subsequent step.

Furthermore, in accordance with the invention, the resultant mixture is heated to a temperature of not less than 50° C., preferably not less than 60° C. and, for still better results, 65° C. to 100° C. to thereby bring the sodium acetate into a transiently molten state. If the heating temperature is too low, the sodium acetate will not be brought into a substantially molten state. On the other hand, the use of an excessively high temperature will not be rewarded with any additional effect desired but rather entails a more than necessary consumption of energy. Where glucose is employed, the heating temperature is preferably set between 60° C. and 80° C.

Moreover, when sodium acetate carries water of crystallization, this water of crystallization functions in the same way as the water which is separately added. Generally when sodium acetate carrying water of crystallization is heated to a temperature beyond 57° C.~59° C., the sodium acetate dissolves in the water of crystallization. When a composition containing sodium acetate is heated, the sodium acetate dissolves, at least in part, in the water of crystallization and/or in the water added separately. In this specification, achieving this condition is referred to as 'to bring sodium acetate into a molten state'.

In the method producing Component A of the invention, there is no limitation on the order of mixing sodium chloride, potassium chloride, calcium chloride, magnesium chloride, sodium acetate, glucose and water and any known ordinary mixing method can be employed. However, as a mixer for use in the mixing of these ingredients, a double-can type equipment, which is capable of heating the charge indirectly with an external steam source and can be used for drying purposes as well, can be employed with advantage.

The following procedures are recommended for an efficient formation of a coating layer of electrolyte compounds except sodium chloride on the surface of grains of sodium chloride.

(1) Potassium chloride is dissolved in a specified amount of water to prepare a concentrated potassium chloride solution. There is no particular limitation on the amount of water to be used here but in terms of procedural efficiency, it is preferable to use about 10~50 parts by weight, preferably about 20 parts by weight, of water based on 100 parts by weight of sodium acetate which is subsequently added. If the required amount of potassium chloride cannot be completely dissolved, a necessary minimum amount of water may be supplementally added.

(2) In the above concentrated potassium chloride solution are dissolved calcium chloride and magnesium chloride so that the potassium chloride will separate out from the solution to yield a potassium chloride suspension.

(3) This potassium chloride suspension is mixed with sodium chloride. This can be advantageously carried out by heating sodium chloride in a mixer at a temperature of not less than 40° C. in the first place, then adding said potassium chloride suspension and stirring the whole mixture.

From the exclusive consideration of the ease of mixing, it might be considered preferable to mix sodium chloride with a solution containing potassium chloride, calcium chloride and magnesium chloride in lieu of said potassium chloride suspension. However, since the solubility of potassium chloride is low as compared with calcium chloride and magnesium chloride, a large amount of water is required for dissolving all of these ingredients. In contrast, the potassium chloride suspension can be prepared with a smaller amount of water and, therefore, facilitates subsequent drying. Moreover, since the suspension obtained by dissolving calcium chloride and magnesium chloride in a concentrated solution of potassium chloride is characterized by the remarkable fineness of the potassium chloride particles separating out, it can be easily blended just like a solution.

(4) The resultant mixture is dried, if required, to adjust the water content and, then, mixed with sodium acetate. For this purpose, the amount of water is preferably adjusted to about 20 parts by weight based on 100 parts by weight of sodium acetate to be added. After addition of sodium acetate, the temperature of the resultant mixture is maintained at not less than 50° C., preferably not less than 60° C., whereupon the sodium acetate is brought into a molten state, with the result that the mixture gains in viscosity to form granules.

In the method of producing Component A of the invention, acetic acid is further added to the granules obtained as in the above stage (4). Drying the granules either before or after addition of acetic acid provides a free-flowing granular to fine-granular powder (granules or fine granules).

Glucose, where it is used, is preferably added in the above stage (4) or in the stage where acetic acid is added, from the standpoint of improved dispersibility of glucose and improved granulation effect.

In the process of producing Component A of the invention, sodium acetate is brought into a molten state to form a uniform dispersion with the trace electrolyte compounds such as calcium chloride, potassium chloride and magnesium chloride as well as glucose, if used, and the sodium acetate including these small amounts of electrolytes adheres to the surface of crystal grains of sodium chloride to form a coating layer, which in turn acts as a binder to bind pluralities of sodium chloride crystal grains together, thus providing granules (or fine granules).

Then, by dissolving the Component A of the invention and Component B in an appropriate amount of water, there can be obtained a bicarbonate dialyzate.

For reference, the concentrations of respective electrolyte compounds (ions) in the conventional bicarbonate dialyzate are shown in Table 2.

TABLE 2

| | |
|---|---|
| $Na^+$ | 120~145 mEq/l |
| $K^+$ | 1~4 mEq/l |
| $Ca^{2+}$ | 1~4 mEq/l |
| $Mg^{2+}$ | 0.5~2 mEq/l |
| $Cl^-$ | 90~140 mEq/l |
| $CH_3COO^-$ | 2~14 mEq/l |
| $HCO^{3-}$ | 15~40 mEq/l |
| Glucose | 0~2.5 g/l |

EFFECTS OF THE INVENTION

By the production process of the invention, a granular to fine-granular dry mix powder (Composition A) can be obtained, without resort to any special granulation procedure, by forming a coating layer comprising trace electrolyte compounds on the surface of the crystal grains of sodium chloride and letting this coating layer act as a binder to join grains of sodium chloride together into granules or fine granules. Furthermore, by the production method of the invention, said coating and granulation can be accomplished using a simple mixing device, without requiring any of the conventional dry-granulating machine, wet-granulating machine and coating machine, and, moreover, a dry mix product of uniform composition can be produced in large quantities and at low cost.

Furthermore, as a consequence, the risk of contamination with foreign matter owing to friction with the equipment can be decreased.

Since Component A of the invention is a dry mix powder which is light in weight, small in volume and uniform in composition, the transportation cost as well as the storage space requirements in hospitals, etc. can be decreased while an acceptable quality (uniformity of composition of electrolyte compounds) equivalent to that of the conventional liquid composition is maintained. Furthermore, since a simple packaging material can be employed for shipment, the invention is not only of value for medical institutions but also useful for the society at large as a means for solving the problem associated with the disposal of polyethylene bottles or equivalent containers.

EXAMPLES

The following examples and comparative examples are intended to further illustrate the characteristics and usefulness of the present invention.

Component A was invariably produced according to the electrolyte ion formula of Component A shown in Table 3.

TABLE 3

| | |
|---|---|
| $Na^+$ | 135 mEq/l |
| $K^+$ | 2.5 mEq/l |
| $Ca^{2+}$ | 3.5 mEq/l |
| $Mg^{2+}$ | 1.5 mEq/l |
| $Cl^-$ | 106.5 mEq/l |
| $CH_3COO^-$ | 8.5 mEq/l* |
| $HCO^{3-}$ | 30 mEq/l |

*The amount indicated includes the amount of $CH_3COO^-$ (2.5 mEq/l) derived from glacial acetic acid which is added as a pH control agent in using Component A (blending Component A with Component B).

Example 1

The starting materials (1000 kg) shown in Table 4 were used.

TABLE 4

| | |
|---|---|
| Sodium chloride | 823.69 kg |
| Potassium chloride | 26.53 kg |
| Calcium chloride | 36.63 kg |
| Magnesium chloride | 21.71 kg |
| Sodium acetate | 70.07 kg |
| Acetic acid | 21.37 kg |

First, a double-can mixer (steam heating type) was charged with 823.69 kg of sodium chloride and the charge was heated to 68° C. with constant stirring. Then, 26.53 kg of potassium chloride was added. This was further followed by addition of 36.63 kg of calcium chloride and 21.71 kg of magnesium chloride and the whole charge was mixed under heating. The mixer was further charged with 17 l of pure water (24 parts by weight based on 100 parts by weight of sodium acetate to be added next) and 70.07 kg of sodium acetate and the whole charge was mixed under heating.

Fifteen (15) minutes after addition of sodium acetate, the charge gained in whiteness a little. As the heating and mixing were further continued, the charge developed a characteristic viscosity and the grains began to adhere to each other. As the heating and mixing were further continued for 1 hour, the charge became dry to provide a free-flowing granular to fine-granular powder. After this powder was cooled, 21.37 kg of acetic-acid was added and the mixing was continued for an additional 30 minutes, after which 983 kg of product was recovered.

From this product, 5 random samples (n1, n2, n3, n4 and n5) were taken and tested. The test was carried out as follows. Each sample, 7.024 g, was dissolved in water and, then, 2.52 g of sodium bicarbonate was dissolved to make 350 ml. The electrolyte ion concentrations of the samples were then measured. The results are shown in Table 5. The concentrations of the electrolyte ions, namely $Na^+$, $K^+$, $Ca^{2+}$, $Mg^{2+}$, $Cl^-$ and $CH_3COO^-$, were determined using Dionex ion chromatograph.

TABLE 5

| | Ion concentrations (Unit: Eq/l) | | | | | |
|---|---|---|---|---|---|---|
| | $Na^+$ | $K^+$ | $Ca^{2+}$ | $Mg^{2+}$ | $Cl^-$ | $CH_3COO^-$ |
| n1 | 135.4 | 2.56 | 3.50 | 1.52 | 106.2 | 8.6 |
| n2 | 135.0 | 2.44 | 3.41 | 1.45 | 107.6 | 8.6 |
| n3 | 134.6 | 2.53 | 3.40 | 1.44 | 107.0 | 8.5 |
| n4 | 134.0 | 2.42 | 3.47 | 1.48 | 107.6 | 8.7 |
| n5 | 136.5 | 2.46 | 3.55 | 1.46 | 107.4 | 8.7 |
| Mean | 135.10 | 2.482 | 3.466 | 1.470 | 107.16 | 8.62 |
| SD | 0.938 | 0.060 | 0.063 | 0.032 | 0.590 | 0.084 |

<SD: standard deviation (the same applies hereinafter)>

Example 2

The starting materials (1000 kg) shown in Table 4 were used.

First, a double-can mixer (steam heating type) was charged with 823.69 kg of sodium chloride and the charge was heated to 70° C. with constant stirring. On the other hand, 26.53 kg of potassium chloride was dissolved in 85 l of pure water and, then, 36.63 kg of calcium chloride and 21.71 kg of magnesium chloride were dissolved to provide a suspension of fine crystals of potassium chloride. This suspension was fed to the mixer containing the sodium chloride and the mixing and heating were continued to dry the charge. In this stage, the water content of the charge was measured and when the water content had become 1.85%, 70.07 kg of sodium acetate was added to the charge (temperature 82° C.), followed by mixing and heating (the water content was 27 parts by weight based on 100 parts by weight of sodium acetate).

Fifteen (15) minutes after addition of sodium acetate, the charge gained in whiteness a little. As the heating and mixing were further continued, the charge developed a characteristic viscosity and the grains began to adhere to each other. As the heating and mixing were further continued for 1.5 hours, the charge became dry to provide a free-flowing granular to fine-granular powder. After this powder was cooled, 21.37 kg of acetic acid was added and the mixing was continued for an additional 30 minutes, after which 976 kg of product was recovered.

From this product, 5 random samples (n1, n2, n3, n4 and n5) were taken and tested. The test was carried out as follows. Each sample, 7.024 g, was dissolved in water and, then, 2.52 g of sodium bicarbonate was dissolved to make 350 ml. The electrolyte ion concentrations of the samples were then measured. The results are shown in Table 6. The concentrations of the electrolyte ions, namely $Na^+$, $K^+$, $Ca^{2+}$, $Mg^{2+}$, $Cl^-$ and $CH_3COO^-$, were determined using Dionex ion chromatograph.

TABLE 6

| | Ion concentrations (Unit: Eq/l) | | | | | |
|---|---|---|---|---|---|---|
| | $Na^+$ | $K^+$ | $Ca^{2+}$ | $Mg^{2+}$ | $Cl^-$ | $CH_3COO^-$ |
| n1 | 135.8 | 2.52 | 3.44 | 1.48 | 107.5 | 8.6 |
| n2 | 136.3 | 2.46 | 3.47 | 1.45 | 106.4 | 8.6 |
| n3 | 135.1 | 2.46 | 3.48 | 1.53 | 107.2 | 8.7 |
| n4 | 136.5 | 2.53 | 3.45 | 1.51 | 106.8 | 8.6 |
| n5 | 135.4 | 2.55 | 3.49 | 1.50 | 107.2 | 8.6 |
| Mean | 135.82 | 2.504 | 3.466 | 1.494 | 107.02 | 8.62 |
| SD | 0.589 | 0.045 | 0.021 | 0.031 | 0.427 | 0.045 |

Example 3

The starting materials (1213.55 kg) shown in Table 7 were used. In this example, Component A was produced according to the formula of electrolyte ion concentrations shown in Table 1 and a glucose concentration of 1.5 g/l.

TABLE 7

| Sodium chloride | 823.69 kg |
|---|---|
| Potassium chloride | 26.53 kg |
| Calcium chloride | 36.63 kg |
| Magnesium chloride | 21.71 kg |
| Sodium chloride | 70.07 kg |
| Acetic acid | 21.37 kg |
| Glucose | 213.55 kg |

First, a double-can mixer (steam heating type) was charged with 823.69 kg of sodium chloride and the charge was heated to 73° C. with constant stirring. Then, 26.53 kg of potassium chloride was added. This was further followed by addition of 36.63 kg of calcium chloride and 21.71 kg of magnesium chloride and the whole charge was mixed under heating. The mixer was further charged with 17 l of pure water (24 parts by weight based on 100 parts by weight of sodium acetate to be added next) and 70.07 kg of sodium acetate and the whole charge was mixed under heating.

Fifteen (15) minutes after addition of sodium acetate, the charge gained in whiteness a little. As the heating and mixing were further continued, the charge developed a characteristic viscosity and the grains began to adhere to each other. Then, 213.55 kg of glucose was added and the heating and mixing were further continued, whereby the system gained further in viscosity. Then, the system dried up to give a free-flowing granular to fine-granular powder. After this powder was cooled, 21.37 kg of acetic acid was added and the mixing was continued for an additional 30 minutes, after which 1191 kg of product was recovered.

From this product, 5 random samples (n1, n2, n3, n4 and n5) were taken and tested. The test was carried out as follows. Each sample, 8.524 g, was dissolved in water and, then, 2.52 g of sodium bicarbonate was dissolved to make 350 ml. The electrolyte ion concentrations of the samples were respectively measured. The results are shown in Table 8. The concentrations of the electrolyte ions, namely $Na^+$, $K^+$, $Ca^{2+}$, $Mg^{2+}$, $Cl^-$ and $CH_3COO^-$, and glucose were determined using Dionex ion chromatograph.

TABLE 8

| | Ion and glucose concentrations (Unit: Eq/l) | | | | | | |
|---|---|---|---|---|---|---|---|
| | $Na^+$ | $K^+$ | $Ca^{2+}$ | $Mg^{2+}$ | $Cl^-$ | $CH_3COO^-$ | Glucose |
| n1 | 135.4 | 2.56 | 3.50 | 1.52 | 106.2 | 8.6 | 1.52 g/l |
| n2 | 135.0 | 2.44 | 3.41 | 1.45 | 107.6 | 8.6 | 1.50 g/l |
| n3 | 134.6 | 2.53 | 3.40 | 1.44 | 107.0 | 8.5 | 1.51 g/l |
| n4 | 134.0 | 2.42 | 3.47 | 1.48 | 107.6 | 8.7 | 1.48 g/l |
| n5 | 136.5 | 2.46 | 3.55 | 1.46 | 107.4 | 8.7 | 1.50 g/l |
| Mean | 135.10 | 2.482 | 3.466 | 1.470 | 107.16 | 8.62 | 1.502 g/l |
| SD | 0.938 | 0.060 | 0.063 | 0.032 | 0.590 | 0.084 | 0.015 |

The Component A (product) obtained in each of Examples 1–3 was a free-flowing granular to fine-granular powder which remained stable for a long time. The test results (Tables 5, 6 and 8) indicated that all of the products were very much uniform in composition. Thus, the concentrations of electrolyte ions in an aqueous solution of each Composition A were within the practically acceptable ranges of deviation from the standard electrolyte ion formula (Table 3) and the variation (SD) between samples for each electrolyte ion concentration was extremely small.

Comparative Example 1

The starting compounds (1000 kg) shown in Table 4 were mixed without pure water to prepare 975 kg of a mixed powder. In this process, said coating and granulation mediated by sodium acetate did not take place and the resultant composition contained blocks apparently comprised of calcium chloride and magnesium chloride. Moreover, it was a somewhat moist powder which caked in 1 week when stored at room temperature.

Reference Example 1

A microphotograph (magnification×20) of the Component A (product) obtained in Example 1 is shown in FIG. 1.

Figure 2:
FIG. 2 is a microphotograph showing an artificial kidney perfusion component for preparation of bicarbonate dialyzate as prepared by the conventional method.

A microphotograph (magnification×20) of the mixed powder of Comparative Example 1 is shown in FIG. 2.

Reference Example 2

The particle size distribution of the Component A (product) of Example 1 and that of the mixed powder of Comparative Example 1 are shown in Table 9.

TABLE 9

| | Particle size distribution (weight %) | |
|---|---|---|
| Mesh size | Example 1 | Comparative Example 1 |
| Plus No. 10 sieve | 0 | 0 |
| Minus No. 10, on No. 12 | 1.6 | 0.1 |
| Minus No. 12, on No. 18 | 12.7 | 0.3 |
| Minus No. 18, on No. 30 | 52.5 | 12.6 |
| Minus No. 30, on No. 42 | 25.7 | 58.9 |
| Minus No. 42, on No. 83 | 7.2 | 24.7 |
| Minus No. 83 sieve | 0.3 | 3.4 |

We claim:

1. A method of producing an artificial kidney perfusion component for the preparation of an artificial kidney perfusion fluid for bicarbonate dialysis, which is a dry mix powder comprising sodium chloride, potassium chloride, calcium chloride, magnesium chloride and sodium acetate as electrolyte compounds, the method comprising mixing said electrolyte compounds in the presence of not less than 10 parts by weight of water (inclusive of the water crystallization when the water of crystallization is bound to sodium acetate) based on 100 parts by weight of sodium acetate (as anhydride) to produce a mixture, heating the resultant mixture at a temperature of 50° C. to 100° C. to bring the sodium acetate into a transiently molten state and to make the mixture gain in viscosity and form granules, and adding acetic acid to said mixture.

2. A method of producing an artificial kidney perfusion component for bicarbonate dialysis as claimed in claim 1 which comprises heating a mixture of electrolyte compounds as obtained at a temperature of not less than 60° C.

3. A method of producing an artificial kidney perfusion component for bicarbonate dialysis as claimed in claim 1 which comprises mixing glucose together with said electrolyte compounds.

4. A method of producing an artificial kidney perfusion component for bicarbonate dialysis as claimed in claim 3 wherein the mixing of glucose together with said electrolyte compounds is performed either before or after the sodium acetate is brought into a molten state.

5. A method of producing an artificial kidney perfusion component for bicarbonate dialysis as claimed in claim 3 wherein a mixture of electrolyte compounds and glucose as obtained is heated at a temperature of not less than 60° C.

6. A method of producing an artificial kidney perfusion component for bicarbonate dialysis as claimed in claim 3 wherein the mixing of glucose with the electrolyte compounds is performed in the presence of 20 to 70 parts by weight of water based on 100 parts by weight of sodium acetate.

7. A method of producing an artificial kidney perfusion component for bicarbonate dialysis as claimed in claim 1 which comprises mixing said electrolyte compounds in the presence of 20 to 70 parts by weight of water based on 100 parts by weight of the sodium acetate.

8. A method of producing an artificial kidney perfusion component for the preparation of an artificial kidney perfusion fluid for bicarbonate dialysis as claimed in claim 10, the method comprising (1) a stage in which potassium chloride is dissolved in a specified amount of water to produce a concentrated potassium chloride solution, (2) a stage in which calcium chloride and magnesium chloride are dissolved in the concentrated potassium chloride solution to cause precipitation of said potassium chloride to produce a potassium chloride suspension, (3) a stage in which the potassium chloride suspension is mixed with sodium chloride with heating to produce a mixture, and (4) a stage in which the mixture is mixed with sodium acetate in the presence of 10 to 130 parts by weight of water (inclusive of the water of crystallization when the water of crystallization is bound to sodium acetate) based on 100 parts by weight of sodium acetate (as anhydride) to produce a mixture, the resulting mixture is heated at a temperature of 50° C. to 100° C. to bring the sodium acetate into a transiently molten state and to make the mixture gain in viscosity and form granules, and the mixture is mixed with acetic acid.

9. An artificial kidney perfusion component for bicarbonate dialysis in the form of granules or fine granules each comprised of a plurality of grains of sodium chloride carrying a compositionally uniform coating of potassium chloride, calcium chloride, magnesium chloride and sodium acetate on the surface.

* * * * *